United States Patent [19]

Levine et al.

[11] Patent Number: 5,218,139
[45] Date of Patent: Jun. 8, 1993

[54] METHOD FOR INHIBITING IGE PRODUCTION

[75] Inventors: Alan D. Levine, Ballwin, Mo.; Paul W. Collins, Deerfield, Ill.

[73] Assignee: G. D. Searle & Co., Chicago, Ill.

[21] Appl. No.: 892,870

[22] Filed: Jun. 3, 1992

Related U.S. Application Data

[62] Division of Ser. No. 635,000, Dec. 27, 1990, Pat. No. 5,157,052.

[51] Int. Cl.$^5$ .......................................... C07C 177/00
[52] U.S. Cl. ...................................................... 560/121
[58] Field of Search ........................................ 560/121

[56] References Cited

U.S. PATENT DOCUMENTS

| | | | |
|---|---|---|---|
| 3,965,143 | 6/1976 | Collins et al. | 260/468 |
| 4,059,587 | 11/1977 | Smith et al. | 260/301 |
| 4,087,621 | 5/1978 | Collins et al. | 560/231 |
| 4,312,994 | 1/1982 | Collins | 560/121 |
| 4,322,543 | 3/1982 | Collins et al. | 556/436 |
| 4,935,446 | 6/1990 | Imaki et al. | 514/530 |

OTHER PUBLICATIONS

Chouaib, Salem et al. Prostaglandins E As Modulators Of The Immune etc. Lymphokine Research vol. 7, No. 3 Jan. 1988.
Collins, P. W. et al. Synthesis And Gastric Antisecretory Properties etc. J. Med. Chem 20 1152 Jan. 1977.
Collins, P. W. et al. Synthesis And Gastric Antisecretory Properties etc. J. Med. Chem 29 1195 Jan. 1986.
Collins, P. W. et al 18-Cycloalkyl Analogues Of Enisoprost J. Med. Chem 32 1001 Jan. 1989.
Finkleman, F. D. et al. Suppression In Vivo Polyclonal IgE Responses etc. Proc. Natl. Acad. Sci. USA 83 9675 Jan. 1986.
Galizzi, J-P et al IFN-gamma And Prostaglandin E2 Inhibit etc. J. Immunol. 141 1982-1988.
Koopman, W. J. et al Prostaglandin Inhibition Of The Immunologic etc. Proc. Soc. Exper. Biol. Med. 137 64 Jan. 1971.
Collins, P. W. et al Synthesis And Gastric Antisecretory Properties etc. J. Med. Chem. 26 786 Jan. 1983.
McLeish, K. R. et al. Serial Changes In Humoral And Cellular etc. J. Lab. Clin. Med. 106 517 Jan. 1985.
Pene, Jerome et al IgE Production By Normal Human Lymphocytes Is etc. Proc. Natl. Acad. Sci. USA 85 6880 Jan. 1988.
Roper, Rachel et al Prostaglandin E2 Promotes IL-4-Induced IgE And etc. J. Immunol 145 2644 Jan. 1990.
Rousset, Francoise Regulation of Fc Receptor For IgE (CD23) And etc. J. Immunol. 140 2625 Jan. 1988.
Goodwin Prostaglandins 33 (Suppl) 61-7 Jan. 1987.
Reinmann Prostaglandins 33 (Suppl) 105-118 Jan. 1987.

*Primary Examiner*—Robert Gerstl
*Attorney, Agent, or Firm*—Roger A. Williams; Paul D. Matukaitis

[57] ABSTRACT

A method is described for inhibiting IgE production which comprises administering, in an amount effective to inhibit IgE production, a prostaglandin of the formula:

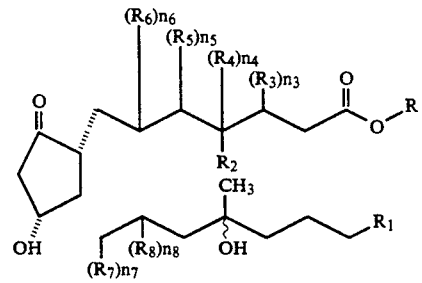

or a pharmaceutically acceptable non-toxic salt thereof, in which R is hydrogen, $C_1$–$C_5$ alkyl, $C_3$–$C_8$ cycloalkyl, phenyl, or mono, di- or tri-substituted phenyl in which the substituents are selected form the group consisting of bromo, chloro, fluoro, iodo, $C_1$–$C_5$ alkyl, hydroxy, nitro, acetyl, alkoxy, carboxy, acetoxy, amino, mono- or di- alkyl amino, amido and acetamido; $R_1$ and $R_2$ independently are hydrogen or $C_1$–$C_5$ alkyl, $n_3$, $n_4$, $n_5$, $n_6$, $n_7$, and $n_8$ independently are zero or one; when n's are zeros, $R_3$ and $R_4$ together, $R_4$ and $R_5$ together, $R_5$ and $R_6$ together, and $R_7$ and $R_8$ together are double bonds; when n's are ones, $R_3$, $R_5$, $R_6$, $R_7$ and $R_8$ independently are hydrogen, $R_4$ is hydrogen or methyl, or $R_3$ and $R_4$ together, $R_4$ and $R_5$ together, or $R_5$ and $R_6$ together are methylene.

1 Claim, No Drawings

METHOD FOR INHIBITING IGE PRODUCTION

This is a division of application Ser. No. 07/635,000, filed Dec. 27, 1990, U.S. Pat. No. 5,157,052.

FIELD OF THE INVENTION

This invention relates to a method for inhibiting IgE production by use of prostaglandins.

BACKGROUND

Mammals have evolved a defensive surveillance mechanism, known as the immune system, which protects them from a wide variety of environmental agents such as pathogenic microorganisms (e.g., viruses, bacteria and parasites). The immune system can specifically recognize, immobolize and eliminate environmental agents by way of a cellular-based or immunoglobulin-based response. However, certain human diseases are caused by either an over-reaction or under-reaction of the immune system. Such inappropriate or inopportune immune responses can lead to immunodeficiencies and can lead to autoimmune diseases.

When the immune system recognizes environmental agents as foreign, an undesirable immunopathological disorder can result (hypersensitivity disease), commonly referred to as an allergic reaction. Allergies in man are characterized by the appearance in serum and tissue of immunoglobulins of the immunoglobulin E (IgE) isotype directed against specific environmental agents. More formally, diseases in which the predominant cause can be attributed to the degranulation of tissue mast cells, stimulated by the cross-linking of the IgE receptor by antigen-bound immunoglobulins of the IgE isotype, are classified as atopic disorders (Atopy). Antigen crosslinking of surface-bound IgE molecules leads to an immediate degranulation of the mast cells and release of pre-formed inflammatory mediators, such as histamine and proteolytic enzymes, and subsequent synthesis and secretion of other arachidonic acid metabolites, such as platelet activating factor and leukotrienes, which act as chemoattractants, inflammatory activators and spasmogens for the issue surrounding the site of allergen exposure (J. Morley et al., Mediators of Allergy. In Allergy: Immunological and Clinical Aspects, M. H. Lessof, ed. John Wiley & Sons; Chichester, England: 45-72 (1984). This combination of pharmacological mediators (whose activities also include vasodilation and bronchoconstriction) leads to irritability in nasal passageways resulting in sneezing, running noses, congestion, headaches and watery eyes, all of which are well known symptoms of allergic rhinitis (a sub-class of the disorders collectively called atopy). Atopy includes allergic rhinitis, asthma, food allergies, drug allergies, atopic dermatitis, hyper IgE syndrome and anaphylasix (M. H. Lessof et al. Gastrointestinal reactions and food intolerance. In Allergy: Immunological and Clinical Aspects, M. H. Lessof, ed. John Wiley & Sons; Chichester, England 175-218 (1984). Atopic disorders and similar undesirable immune effects resulting from allergic type reactions cause tissue damage and life threatening conditions.

It is estimated that twenty percent of the North American populations and Western European populations is effected by allergies and asthma alone. Therefore, suppression of undesirable immune effects, such as those associated with the IgE isotype, is paramount to treating patients suffering from various immune related disorders. Current methods for treating patients with immune related disorders are non-specific (e.g., destroy both the desirable and undesirable effects of the immune response) and include dangerous side effects.

Current therapy in allergy is generally divided into three categories. The first category of therapy is directed toward preventing the action of inflammatory mediators, by symptomatic treatment via anti-histamines, systemic bronchodilators, aerosol bronchodilators, systemic corticosteroids, and nasal steroids. The second category of therapy is directed toward generalized immuno suppression with the use of topical or systemic corticosteroids. The third category of therapy is directed toward propylactic desensitization (by repeated injection of impure allergen mixtures) directed toward the stimulation of blocking antibodies (most likely IgG) to neutralize or compete with an IgE response. None of these therapies are specific.

What is needed is a therapy that is specific (i.e., does not interfere with desirable functions of the immune response but hinders the life threatening or tissue damaging aspects of the immune response) for treating undesired immunologic effects. Such an immunosuppressive treatment would benefit patients suffering from the effects of autoimmunity, and hypersensitivity.

Immunosuppressive effects of prostaglandins in vitro has been demonstrated with natural prostaglandin E2 (PGE$_2$) (See J. Pene et al., Proc. Natl. Acad. Sci. USA. 85:6880 (1988). In addition, certain prostaglandins have been disclosed as useful for the treatment of skin diseases such as psoriasis, useful for the prevention of thrombus formation, and useful for stimulating the production of growth hormone and as regulators of the immune response (see U.S. Pat. Nos. 4,155,908 and 4,128,564). Likewise, U.S. Pat. Nos. 4,260,771 and 4,059,587 disclose compounds with prostaglandin-like biological activity that are useful as renal vasodilators, as platelet aggregation inhibitors, and as treatments of certain autoimmune diseases. None of the disclosures, however, teach a method of inhibiting production of IgE.

The present invention provides a highly specific method for treating undesirable effects of the immune response associated with the production of IgE. The method is highly specific in that the method inhibits the IgE response without inhibiting the response of other isotypes.

SUMMARY OF THE INVENTION

The invention is a method for inhibiting IgE production which comprises administering, in an amount effective to inhibit IgE production, a prostaglandin of the formula:

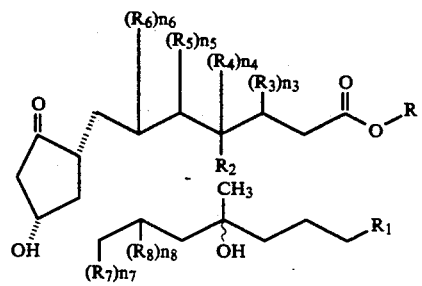

or a pharmaceutically acceptable non-toxic salt thereof, in which R is hydrogen, $C_1$-$C_5$ alkyl, $C_3$-$C_8$ cycloalkyl, phenyl, or mono, di- or tri-substituted phenyl in which the substituents are selected from the group consisting of bromo, chloro, fluoro, iodo, $C_1$–$C_5$ alkyl, hydroxy, nitro, acetyl, alkoxy, carboxy, acetoxy, amino, mono- or di- alkyl amino, amido and acetamido; $R_1$ and $R_2$ independently are hydrogen or $C_1$–$C_5$ alkyl, $n_3$, $n_4$, $n_5$, $n_6$, $n_7$, an $dn_8$ independently are zero or one; when n's are zeros, $R_3$ and $R_4$ together, $R_4$ and $R_5$ together, $R_5$ and $R_6$ together, and $R_7$ and $R_8$ together are double bonds; when n's are ones, $R_3$, $R_5$, $R_6$, $R_7$ and $R_8$ independently are hydrogen, $R_4$ is hydrogen or methyl, or $R_3$ and $R_4$ together, $R_4$ and $R_5$ together, or $R_5$ and $R_6$ together are methylene.

In preferred prostaglandins, R is hydrogen or alkyl, $R_1$ is alkyl, $R_2$ and $T_4$ are hydrogen, $R_4$ is hydrogen or methyl, $n_3$, $n_4$, $n_5$ and $n_6$ are one and $R_3$, $T_5$ and $R_6$ are hydrogen, $n_7$ and $n_8$ are zero indicating a double bond between positions $R_7$ and $R_8$.

Examples of suitable $C_1$–$C_5$ alkyl radicals include methyl, ethyl, propyl, isopropyl, butyl, sec. butyl, isobutyl, tert. butyl and pentyl. Examples of suitable cycloalkyl radicals are cyclopropyl, cyclobutyl, cyclopentyl, cyclohexyl and cyclocyl. Examples of suitable substituted phenyl radicals are 4-chlorophenyl, 2,4-dichlorophenyl, 4-hydroxyphenyl, 4-aminophenyl, 2-methyl-aminophenyl, 3-dimethyl-aminophenyl, 4-carboxylphenyl, 2,4-dinitrophenyl, 4-methoxyphenyl, 4-methylphenyl, 2-propylphenyl, 3,4-diethylphenyl, 4-acetylphenyl, 2,3,4-tichlorophenyl, and 2,4-dihydroxyphenyl.

The prostaglandins of the invention are produced by known methods and are generally prepared as a mixture of steric isomers. Because of the difficulty of producing pure isomers or the difficulty of separating a mixture of isomers, the method of the invention may be carried out using a mixture of the α and β sterochemical configurations of the prostaglandins. It is appreciated, however, that one configuration is considerably more active than the other.

Examples of suitable prostaglandins include (±) phenyl 11α, 16-dihydroxy-16-methyl-9-oxoprosta-3,5Z,13E-trien-1-oate, (±)methylethyl 2-[2-[3R-3α-hydroxy-2β-(4-hydroxy-4-methyl-1E-octenyl)-5-oxo-1α-cyclopentyl]ethylcyclopropanepropanoate, (±) ethyl 11α,16-dihydroxy-16-methyl-9-oxoprosta-5Z, 13E-dien-1-oate, (±) 4-methoxyphenyl 2-([3R-3α-hydroxy-2β-(4-hydroxy-4-methyl-1E-octenyl)-5-oxo-1α-cyclopentyl]-methyl-1-cyclopropanebutanoate, (±) propyl 11α, 16-dihydroxy-16-methyl-90-oxoprost-13E-en-1-oate, (±)phenyl 11α, 16-dihydroxy-4,4,16-trimethyl-9-oxoprost-13E-en-1-oate, (±) phenyl 20-ethyl-11α, and 16-dihydroxy-16-methyl-9-oxoprost-13E-en-1-oate, and (±) ethyl 11α, 16-dihydroxy-16-methyl-9-oxoprosta-4Z, 13E-dien-1-oate.

One embodiment of the invention is directed to (±) methyl 20-ethyl-11α, 16-dihydroxy-16-methyl-9-oxoprost-13E-en-1-oate which exhibits excellent IgE inhibition and is essentially free of detrimental diarrhea side effects.

As used herein, IgE production is indicated by and associated with those effects resulting from inappropriate or untimley production of IgE, which production leads to eczema, asthma, food allergies, drug allergies, and symptoms like sneezing, running noses, congestion, headaches, and watery eyes. Ig refers to Immunoglobulin, which is a globular protein that has antibody activity. The E, G, A, M or D that follows the Ig prefix refers to the class of immunoglobulin. Further, as used herein, an amount effective to inhibit IgE production is that amount which alleviates or prevents the undesired effects indicated by IgE production without causing greater undesirable effects than the IgE response. In addition, the "(±)" symbol before the compounds indicates the racemic forms and the wavy line represents the alternate α or β configuration, which α or β diastereoisomers are separable by high performance liquid chromatography (HPLC). The broken line indicates the substituent attached is behind the ring plane (i.e., α configuration). The wedge indicates the substituent attached is in front of the ring plane (i.e., β configuration).

Generally, the compounds for use in the method of the invention are well known and procedures for their synthesis are readily available. For example, U.S. Pat. Nos. 4,087,621; 4,322,543; 4,312,994; 3,965,143; and J. Med. Chem. volumes 20, 26 and 29 teach how to make the compounds of this invention.

It has been found that in vitro assays for prostaglandins for IgE inhibition is not predictive of biological activity in vivo. For example, natural prostaglandins $E_1$ and $E_2$ exhibit inhibition of IgE in vitro but exhibits only low inhibition in vivo. Thus, the method of the invention includes a class of synthetic prostaglandins which exhibits high IgE inhibition in vivo.

Biological testing in vivo demonstrates that the serum IgE response can be inhibited without suppression of serum IgG levels. The assay used to detect inhibition of IgE production by the method of the invention is as follows:

Mouse hybridoma cells expressing either FF1-4D5 antibody or HδA1 antibody are thawed, established in culture, and incubated in mice as ascite tumors. FF1-4D5 antibody is a mouse IgG2a monoclonal antibody of the b allotype that binds the Fd fragment of the ∂ chain of the a allotype IgD which activates β cells through antigen internalization and processing, promoting cognate interactions with antigen-specific T cells (D. K. Goroff et al., J. Immunol, 136:2382 (1986)). HδA1 antibody is a mouse IgG2b of the b allotype that binds the Fc fragment of the ∂ chain of the a allotype IgD which activates β cells through crosslinking IgD (I. M. Zitron and B. L. Clevinger, J. Exp. Med. 152:1135 (1980)). Each antibody is purified from their respective ascites tumor fluid. While each antibody alone does not stimulate immunoglobulin synthesis in vivo, Ig production increases when a mixture of FF1-4D5 antibody and HδA1 antibody is injected into mice. Serum from the injected mice is recovered and the mean concentrated of IgE determined. IgE determinations demonstrate that IgE concentration peaks between about 6 and 10 days after injection (about 8 to 40 fold increase).

To demonstrate inhibition of IgE production by the method of the invention, mice are injected with a mixture of FF1-4D5 antibody and HδA1 antibody, and on days 3 and 4 after the injection, compounds are administered in accordance with the method of the invention. Serum levels of IgE are determined and IgE levels are shown to be inhibited in a dose dependent manner.

Sera from mice treated with compounds in accordance with the method of the invention are analyzed for levels of IgG1, IgG2a, IgG3, and IgM. Analysis shows that IgG1, IgG2a, IgG3 and IgM levels are not decreased while at the time IgE levels are decreased.

Although a mouse model was used to measure IgE production and inhibition of IgE production, other models can be used. Examples of other models capable of measuring IgE production and inhibition of IgE production include the guinea pig model, the rabbit aspergillus model, and the helminthic parasite infected mouse model. More specifically, the Nippostrongulus model (F. Finkelman et al., *Proc. Natl. Acad. Sci USA* 83:9675 (1986), rabbit *alternaria tenuis* model (G. Larson et al., *Federation Proceedings* 48:105 (1987), rat antigen specific model (S. Blythe et al., *Am. Rev. Respir. Dis.* 134:1246 (1986), and the guinea pig anaphylaxis model (J. Clausen et al., *Allergy* 40:15 (1985) can be used.

The preferred time for practicing the method of the invention is prior to an IgE response. Therefore, the method of the invention is preferably used prophylactially. However, the method of the invention can be used after the effects of the IgE response are in progress. Prophylactic use also includes practicing the method of the invention several hours to several weeks prior to anticipated exposure to the IgE eliciting agent (e.g. hay fever season), preferably several weeks. The compounds can be administered by a variety of routes, depending on the circumstances.

The compounds for use in the method of the invention can be administered in the form of a pharmaceutical composition comprising one or more of the compounds or pharmaceutically acceptable non-toxic salts thereof in admixture with one or more pharmaceutically-acceptable non-toxic diluents or carriers.

Regardless of the route of administration selected, the compounds of the invention are formulated into pharmaceutically acceptable dosage forms by conventional methods known to those skilled in the art.

The compounds can be administered in such oral dosage forms as tablets, capsules, pills, powders, granules, suspensions, solutions elixirs, or syrups. Such oral pharmaceutical dosage forms employ such ingredients as diluents and carriers, excipients and lubricants such as glucose, lactose, sucrose, corn and potato starch, sodium carboxymethylcellulose, ethyl cellulose, cellulose acetate, powdered gum carboxymethylcellulose, ethyl cellulose, cellulose acetate, powdered gum tragacanth, gelatin, alginic acid, agar, stearic acid, sodium, calcium and magnesium stearates, sodium lauryl sulfate, polyvinylpyrrolidone, sodium citrate, calcium carbonate, dicalcium phosphate; as well as various agents, surfactants, emulsifiers, dispersing agents, flavoring agents and the like. General texts in the field include *Remington's Pharmaceutical Sciences*, Ed. Arthur Osol, 16th edition, 1980, Mack Publishing Co., Easton, Pa.

The compounds can also be administered intravascularly, intraperitoneally, subcutaneously, intramuscularly, or topically, using forms known to the pharmaceutical art. Pharmaceutical compositions adapted for parenteral administration employ diluents and carriers such as water and water-miscible organic solvents such as sesame oil, groundnut oil, aqueous propylene glycol, and N,N'-dimethylformamide. Examples of such pharamceutical compositions include sterile, isotonic, aqueous saline solutions of the compounds for use in the method of the invention which can be buffered with a pharmaceutically acceptable buffer. In general, the preferred form of administration is oral.

An effective but non-toxic quantity of the compound is employed in treatment. The dosage regiment for treatment with the compounds of this invention is selected in accordance with a variety of factors, including the type, age, weight, sex, and medical condition of the patient; and the severity of the condition; the route of administration and the particular compound employed. An ordinarily skilled physician can readily determine the prescribe the effective amount of the compound require to prevent or arrest th progress of the condition. In so proceeding, the physician could employ relatively low doses at first and subsequently increase the dose until a maximum response is obtained. Dosages of the compounds of the invention can be in the range of about 1 μg/kg to 100 μg/kg bodyweight, preferably in the range of about 10–80 μg/kg.

In the pharmaceutical compositions and method of the present invention, the foregoing active ingredients will typically be administered in admixture with suitable pharmaceutical diluents, excipients, or carriers (collectively referred to herein as "carrier" materials) suitably selected with respect to the intended form of administration, that is, oral tablets, capsules, elixirs, syrups, and the like, and consistent with conventional pharmaceutical practices. For example, for oral administration in the form of tablets or capsules, the active drug components may be combined with any oral non-toxic pharamceutically acceptable inert carrier including lactose, starch, sucrose, cellulose, magnesium stearate, dicalcium phosphate, calcium sulfate, and mannitol; for oral administration in liquid form, the active drug components may be combined with any oral non-toxic pharmaceutically acceptable inert carrier including ethanol and the like. Moreover, when desired or necessary, suitable binders, lubricants, disintegrating agents, and coloring agents can also be incorporated in the mixture. Suitable binders include starch, gelatin, natural sugars, corn sweeteners, natural and synthetic gums such as acacia, sodium alginate, carboxymethylcellulose, polyethylene glycol, and waxes. Lubricants for use in these dosage forms include boric acid, sodium benzoate, sodium acetate, and sodium chloride. Disinterators include, without limitation, starch, methylcellulose, agar, benotonite, and guar gum. Sweetening and flavoring agents and preservatives are included where appropriate.

The following examples illustrate the specific embodiments of the invention described herein. As would be apparent to skilled artisans, various changes and modifications are possible and are contemplated within the scope of the invention described.

DESCRIPTION OF THE PREFERRED EMBODIMENTS

Preparation of Compounds for Use in the Method of the Invention

EXAMPLE 1

Preparation of

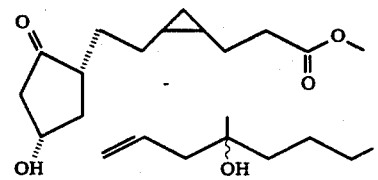

(±) methyl 2-[2-(3R-3α-hydroxy-2β-(4-hydroxy-4-methyl-1E-octenyl)-5-oxo-1α-cyclopentyl]ethyl]cyclopropanepropanoate is as follows:

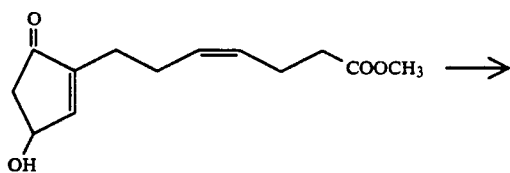

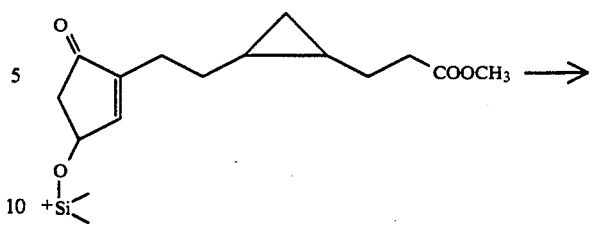

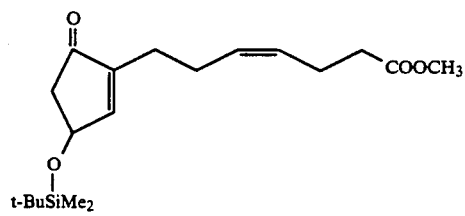

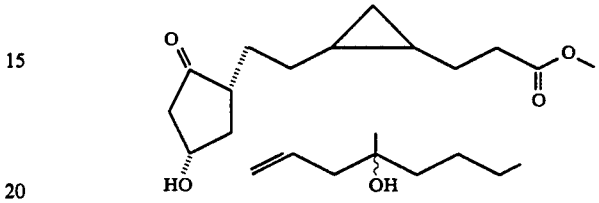

The Δ$^{4,5}$ cis cyclopentenone (Collins et al., J. Med. Chem. 26:786 (1983)) (714 mg 3 mmol) is dissolved in 9 ml of dimethylformamide (DMF) and treated successively with 300 mg of imidazole and 540 mg (3.3 mmol) of t-butyl dimethyl chlorosilane. The reaction mixture is stirred at room temperature for 2 hours, diluted with ether, washed with H$_2$O four times, dried (Na$_2$SO$_4$) and evaporated to an oil which is purified by chromatography (silica gel 10% EtOAc in hexane) to give 928 mg (90% yield) of product as an oil.

Substitution of the above compound into the procedure described for preparation of compound 1b (described in J. Med. Chem., 26:786 (1983)) provides (±) methyl 2-[2-[3R-3α-hydroxy-2β-(4-hydroxy-4-methyl-1E-octenyl)-5-oxo-1α-cyclopentyl] ethyl]cyclopropanepropanoate as a viscous oil. $^1$H NMR (CDCl$_3$):δ0.66 (m, cyclopropane protons); 0.93 (t, C-20); 1.19 (s, C-16 CH$_3$); 4.09 (q, C-11 ).

EXAMPLE 2

Preparation of

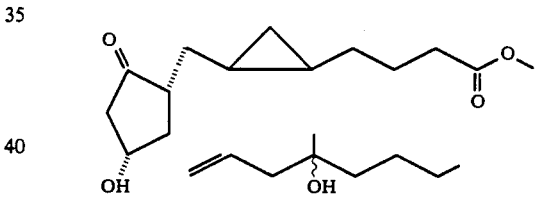

(±) methyl 2-[2-[3R-3α-hydroxy-2β-(4-hydroxy-4-methyl-1E-octenyl)-5-oxo-1α-cyclopentyl]methyl]cyclopropanebutanoate is as follows:

Substitution of Δ$^{5,6}$ cis cyclopentenone

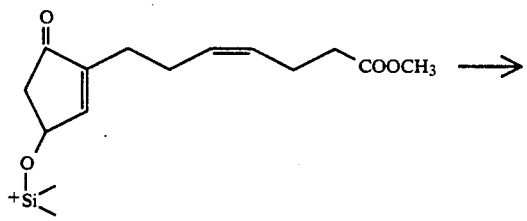

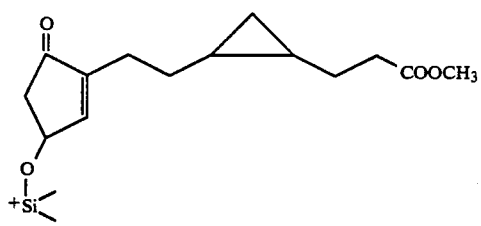

The above cyclopentenone (725 mg, 2.12 mmol) is dissolved in 25 ml of benzene and treated with 3.2 ml of a 2M solution (6.4 mmol) of diethyl zinc (Et$_2$Zn) and 2.7 g (10 mmol) of methylene iodide (CH$_2$I$_2$). The reaction mixture is stirred at room temperature for 48 hours, poured into ether, washed once with a 1N HCl solution, then washed twice with water, dried (Na$_2$SO$_4$) and evaporated. The residue is chromatographed on silica gel (10% EtOAc/hexane) to give 415 mg (55% yield) of product as an oil.

(preparation is described in P. Collins et al., J. Med. Chem. 20:1152 (1977)) into the procedures described above gives (±) methyl 2-[2-[3R-3α-hydroxy-2β-(4-hydroxy-4-methyl-1E-octenyl)-5-oxo-1α-cyclopentyl]-methyl]cyclopropanebutanoate as a viscous oil. $^1$H NMR (CDCl$_3$):δ–0.25 (from TMS) (m, cyclopropane protons); 0.68 (m, cyclopropane protons); 0.93 (t, C-20); 1.18 (s, C-16-CH$_3$; 4.08 (q, C-11).

EXAMPLE 3

Preparation of

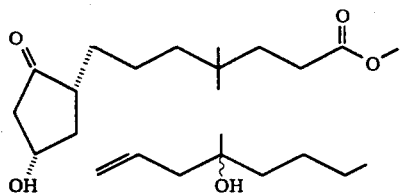

(±) methyl 11α, 16-dihydroxy-4,4,16-trimethyl-9-oxo-prost-13E-en-1-oate is as follows:

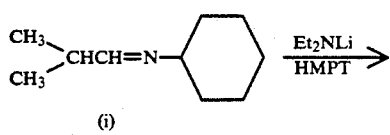

(i)

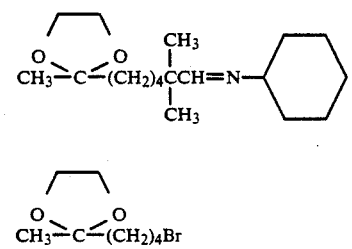

2   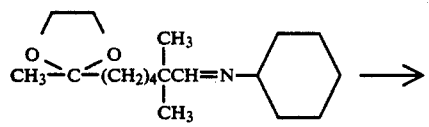

Diethylamine (800 mg, 11 mmol) in 5 ml tetrahydrofuran (THF) is cooled to −60° C. and treated with n-butyl lithium (4.8 ml of a 2.3M solution in hexane, 11 mmol) followed by 2 g of hexamethylphosphoric triamide. The reaction mixture is stirred for 1 hour at −60° C. and then 1.53 g (10 mmol) of the imine (i) (Reference: Cuvigny and Normant, *Bull. Soc. Chim. France* 3976 (1970)) is added in 2 ml of THF. The reaction mixture is stirred for 2 hours at +10° C., cooled to −40° C. and treated with 2.1 g (9 mmol) of the ethylene ketal of 2-keto-6-bromohexane in 2 ml of THF. The reaction mixture is allowed to come to room temperature and to stand overnight. The reaction mixture is diluted with ether, washed twice with H₂O, dried (Na₂SO₄) and evaporated to give 3.2 g of product as an oil.

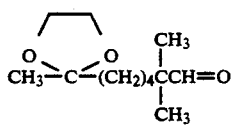

The imine (7 g, 27.7 mmol) is dissolved in 75 ml of THF containing 4.2 ml of glacial acetic acid and allowed to stand at room temperature overnight. The solution is diluted with ether, washed 3 times with H₂O, dried (Na₂SO₄) and evaporated to give 4.7 g (93%) of an oil.

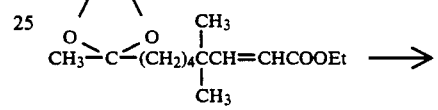

The aldehyde (1.72 g, 10 mmol) and the commercially available phosphine (carboethoxymethylene triphenylphosphorane) (3.93 g, 11 mmol) are dissolved in 25 ml of toluene and refluxed for 24 hours. The solution is cooled, evaporated to a residue (which is taken up in hexane) and filtered (to remove triphenylphosphine oxide), evaporated and chromatographed on silica gel (15% EtOAc/hexane) to give an oil (2.06 g, 80%).

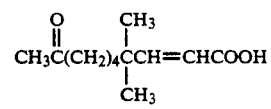

The keto ester (2.06 g, 8 mmol) is dissolved in 30 ml of THF and treated with 10 ml of 1 N HCl solution and allowed to stand at room temperature overnight. The solution is diluted with H₂O and extracted with ether twice. The ether extracts are combined, dried (Na₂SO₄) and evaporated. The residue is taken up in 15 ml of methanol, treated with 6 ml of 2 N NaOH and allowed to stand at room temperature for 48 hours. The solution is diluted with H₂O and extracted with ether to remove neutral materials. The alkaline aqueous solution is acidified in HCl and extracted once with ether and twice with ethyl acetate (EtOAc). The extracts are combined, dried (Na₂SO₄) and evaporated to give 1.6 g (92%) yield) of a yellow oil.

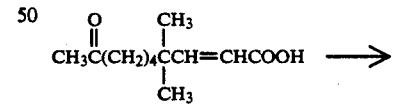

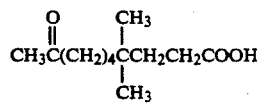

The acid (214 mg, 1 mmol) is dissolved in 25 ml of ethanol and hydrogenated at room temperature and atmospheric pressure using 43 mg of 5% Pd/C as catalyst. The solution is filtered and evaporated to give the saturated acid as an oil.

Substitution of this acid into the procedures described in *J. Med. Chem.*, 29:1198 (1986) for preparation of (±) methyl 7-(3-hydroxy-5-oxo-1-cyclopenten-1-yl)-5(E)-heptenoate provides the hydroxycyclopentenone

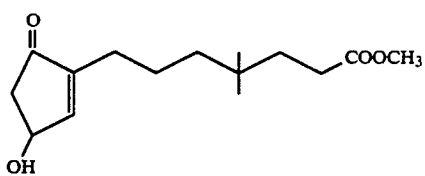

which, when substituted into the procedures for conversion of (±) methyl 7-(3-hydroxy-5-oxo-1-cyclopenten-1-yl)-5(E)-heptenoate to the corresponding prostaglandin, gives (±) methyl 11α, 16-dihydroxy-4,4,16-trimethyl-9-oxoprost-13E-en-1-oate as a viscous oil. $^1$H NMR (CDCl$_3$)δ0.82 (s CH$_3$ groups at C-4); 3.72, (s, OCH$_3$); (4.05 (q, C-11); 5.50, (,, C-13,14).

EXAMPLE 4

Preparation of

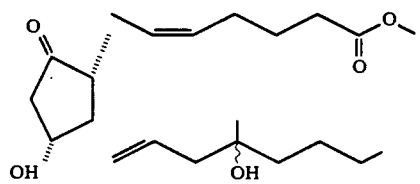

(±) methyl 11α, 16-dihydroxy-16-methyl-9-oxoprosta-5Z, 13E-dien-1-oate is prepared in substantial accordance with the teachings in U.S. Pat. No. 4,087,621 and P. W. Collins et al., *J. of Med. Chem.* 20: 1152 (1977), both publications are incorporated herein by reference.

EXAMPLE 5

Preparation of

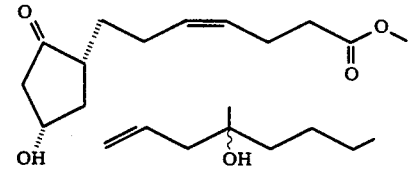

(±) methyl 11α, 16-dihydroxy-16-methyl-9-oxoprosta-4Z, 13E-dien-1-oate is prepared in substantial accordance with the teachings in U.S. Pat. No. 4,322,543 and P. W. Collins et al., *J. of Med. Chem.* 26: 786 (1983), both publications are incorporated herein by reference.

EXAMPLE 6

Preparation of

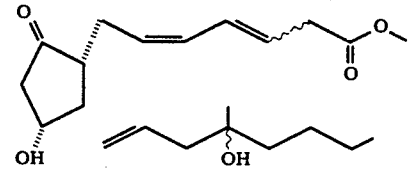

(±) methyl 11α, 16-dihydroxy-16-methyl-9-oxoprosta-3,5Z,13-trien-1-oate is prepared in substantial accordance with the teachings in U.S. Pat. No. 4,312,994 and P. W. Collins et al, *J. of Med. Chem.* 29: 1195 (1986), both publications are incorporated herein by reference.

EXAMPLE 7

Preparation of

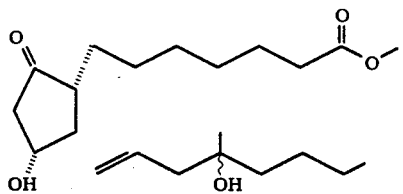

(±) methyl 11α, 16-dihydroxy-16-methyl-9-oxoprost-13E-en-1- oate is in substantial accordance with the teachings in U.S. Pat. No. 3,965,143 and P. W. Collins et al., *J. of Med. Chem.* 20: 1152 (1977), both publications are incorporated herein by reference.

EXAMPLES 8

Preparation of

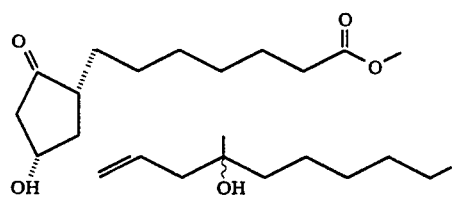

(±) methyl-20-ethyl-11α, 16-dihydroxy-16-methyl-9-oxoprost-13E-en-1-oate is in substantial accordance with the teachings above for making (±) methyl 11α, 16-dihydroxy-16-methyl-9-oxoprost-13E-en-1-oate, with the appropriate omega side chain intermediate employed.

EXAMPLE 9

Preparation of (±) 11α, 16-dihydroxy-16-methyl-9-oxo-prost-13E-en-1-oic acid:

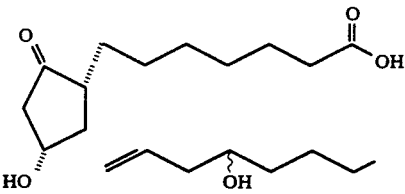

To a stirred suspension of 3.1 g of (±) methyl 11α, 16-dihydroxy-16-methyl-9-oxoprost-13E-en-1-oate in 20 ml Tris buffer (pH 8.0) is added 50 ml porcine liver esterase (Sigma, St. Louis, MO). After 3 hours of stirring at room temperature, the reaction is extracted with 4 portions of ethyl acetate, the extracts combined, dried (Na$_2$SO$_4$), evaporated and chromatographed on silica gel to give 2.8 g of (±) methyl 11α, 16-dihydroxy-16-methyl-9-oxoprost-13E-en-1-oic acid.

EXAMPLE 10

Preparation of (±) 4-(acetylamino)phenyl-11α, 16-dihydroxy-16-methyl-9-oxoprost-13E-en-1-oate:

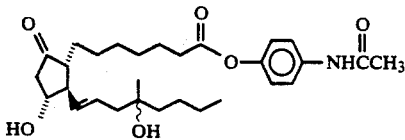

A mixture of 0.37 g (±) 11α, 16-dihydroxy-16-methyl-9-oxoprost-13E-en-1-oic acid, 0.29 ml triethylamine, 0.27 ml isobutylchloroformate in 3.0 ml acetone is cooled to −5° C. A solution of p-acetamidophenol (0.38 g) in 12 ml pyridine is then added and the mixture stirred at room temperature overnight. The mixture is poured into ethyl acetate and washed with successive portions of 1 N HCl, 5% NaHCO$_3$ and dried (Na$_2$SO$_4$). After chromatography on silica gel, 65 mg of the desired product is obtained. $^1$H NMR (CDCl$_3$):δ0.91 (t, CH$_3$); 1.13 (s, CH$_3$); 4.00 (q C-11 H, 6.85–7.6 (aromatic protons).

EXAMPLE 11

Preparation of (±) methylethyl-11α,16-dihydroxy-16-methyl-9-oxoprost-13E-en-1-oate:

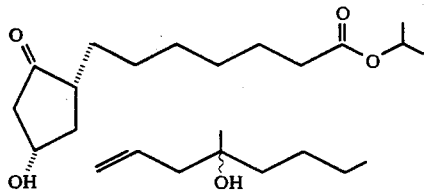

(±) 11α, 16-dihydroxy-16-methyl-9-oxoprost-3E-en-1-oic acid (55 mg) in 3 ml of methylene chloride is treated with 0.25 ml of pyridine, 1 ml of isopropanol and 75 mg of dicyclohexylcarboniimide. The reaction mixture is stirred at room temperature under a nitrogen atmosphere for 48 hours, and then quenched by addition of 0.25 ml of acetic acid. The solvent is evaporated and the residue chromatographed on silica gel (65% ethyl acetate/35% hexane as eluent) to give 19 mg of desired product as a viscous oil. $^1$H NMR (CDCl$_3$): δ1.27 (d, isopropyl CH$_3$'s); 4.08 (q, C-11 H), 5.03 (m, isopropyl CH).

EXAMPLE 12

Preparation of (±) methyl-11α, 16-dihydroxy-16-methyl-9-oxoprostan-1-oate:

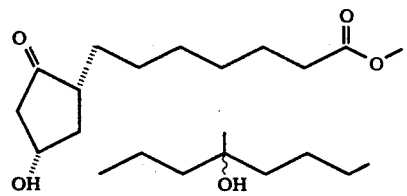

(±) methyl-11α,16-dihydroxy-16-methyl-9-oxoprost13E-en-1-oate (100mg) in 15 ml of ethanol containing 100 mg of 4% palladium on carbon is hydrogenated at room temperature and atmospheric pressure for 24 minutes. The solution is filtered and evaporated. The residue is chromatographed on silica gel (60% ethyl acetate/40% hexane as eluent) to give 86 mg of desired product as a viscous oil. 1H NMR (CDCl$_3$): δ0.93 (t, C.20CH3); 1.18 (d,C.16CH$_3$3.68 (s, OCH$_3$); 4.17 (q C.11 H).

Reagents and Assays

A frozen cell suspension of rat B lymphocyte hybridoma cells (B1E3) as described in A. D. Keegan et al., FASEB Journal V.2, 5541(1988), is rapidly thawed at about 37° C. and mixed drop by drop with 1 ml of supplemented mammalian tissue media containing 95% RPMI (Roswell Park Memorial Institute) 1640 (Gibco, Grand Island, N.Y.), 5% Fetal Calf Serum (Gibco), 1 mM sodium pyruvate (Gibco), and 2 mM glutamine (Gibco). The diluted resuspended cells are collected by centrifugation at 1200 rpm for 5 minutes in a Sorvall RT6000 centrifuge. The spent media is removed by aspiration. The cells are resuspended in 10 ml of the media described above, plated in a CoStar T25 sterile tissue culture flask and incubated at 37° C. in 100% humidity and about 5% carbon dioxide (CO$_2$). When the cells reach a concentration of about $1 \times 10^6$ cells/ml, they are diluted into the same media to a concentration of about $1 \times 10^5$ cells/ml. After about $10 \times 10^6$ cells are available, an ascites tumor is grown in Lou-M rats.

Ten (10) Lou-M rats (Charles River, Wilmington, Mass.) are primed for ascites tumor growth by intraperitoneal injection with about 1 ml of Freunds Incomplete Adjuvant (Gibco, Grand Island, N.Y.). 7–10 days later about $1 \times 10^6$ B1E3 hybridoma cells are inoculated into the primed rats intraperitoneally. After 6–11 days a solid tumor is seen in the rats. The ascites fluid is removed with a 5 ml syringe affixed to a 18 gauge needle. Cells are removed by centifugation.

Monoclonal antibodies are generally purified by chromatography over protein G Sepharose. Ascites fluid is stored frozen at −40° C. until needed. The ascites is thawed at 2°–8° C. and diluted with 9 volumes of 0.02 M Na$_2$HPO$_4$, pH 8.5. The diluted ascites is stirred at 2°–8° C. for 1 hour. If a precipitate is visible, the solution is centrifuged at 23,000× g in a GSA (Sorval) rotor for 1 Hour. The supernatant is decanted and filtered through a 0.2 micron cellulose acetate filter (Amicon, Lexington, Mass.).

The filtered column feed is then passed over a column of protein G Sepharose that has been equilibrated with 0.02 M Na$_2$HPO$_4$ buffer, pH 8.5. Capacity is approximately 5 ml of diluted ascites per ml of protein G Sepharose. After loading the column is washed with 0.02 M Na$_2$HPO$_4$ buffer, pH 8.5 until absorbance at 280 nm returns to baseline. The antibody is eluted from the protein G Sepharose by washing the column with 0.1 M glycine/HCl buffer, pH 2.7. Fractions showing absorbance at 280 nm are adjusted to pH 7with 1 M Tris base. Fractions are pooled and dialyzed against 50 nM phosphate buffered saline, pH 7.0. Purity of purified antibodies is checked by Sodium dodecyl sulfate-polyacrylamide gel electrophoresis (SDS PAGE). Protein is determined using absorbance at 280 nm, assuming an $E^1\% = 14$.

Alternatively, monoclonal antibodies can be purified by chromatography over Baker ABx resin. ABx resin (40 micron particle size) is swelled in 1 M potassium phosphate buffer, pH 7.0, packed into an Amicon 2.2 cm column to give a bed height of 10 cm. The column is then washed with 5 column volumes of 1 M potassium phosphate buffer, pH 7.0, 10 column volumes of distilled water, 10 column volumes 1 M HOAc, and then washed exhaustively with 10 mM MES buffer, pH 5.6 (Sigma, St. Louis, Mo.).

Ascites is diluted with 9 volumes of 10 mM MES buffer, pH 5.6 and gently mixed at 2°–8° C. for 1 hour. Precipitate is removed by centrifugation in a GSA rotor at 23,000×g for 30 minutes and filtered through a 0.2 micron cellulose acetate filter. The filtered solution is applied to the equilibrated column of ABx resin. After loading, the column is washed with 10 mM MES, pH 5.6 until absorbance at 280 nm returns to baseline.

Elution of bound material is effected with a gradient of 100 mL mM MES pH 5.6 to 100 mL 1M $NH_4OAc$. Flow rate is approximately 0.8 mL/min, and 12–15 ml fractions are collected during elution. Fractions are analyzed by SDS PAGE, and pooled based on qualitative assessment of antibody purity and dialyzed as described above. The antibody is concentrated to about 1 mg/ml in an Amicon stirred cell with a YM10 filter (Amicon, Lexington, Mass.) at 4° C. An absorbance of 1.4 at 280 nm in a 1 cm cell is equal to 1.0 mg/ml.

A murine IgE (known as anti-DNP-IgE, as described by Liu et al., *J. Immunol.* 124:2728 (1980) is purified as described above. The IgE standard is stored in phosphate buffered saline (PBS) with 2% newborn Calf Serum (Gibco, Grand Island, N.Y.) at −80° C. at 25 $\mu$/ml.

A frozen cell culture of rat B lymphocyte hybridoma cells (R1E4) (also referred to as 84-1c as described in M. Baniyash et al., *Mol. Immunol.* 25:705 (1988)) is thawed and expanded as described above. About $10 \times 10^6$ cells are injected into nude mice (Charles River, Wilmington, Mass.) as described above. The mice are primed seven days in advance with 1 ml intraperitoneal injection of pristane. R1E4 antibody is purified as described above. About 2 mg/ml solution of R1E4 antibody is added to a Spectra/por molecular porous tubing membrane (molecular weight cut-off 12,000–14,000) and sealed with Spectrum clips (Spectrum Medical Industries, Inc., Los Angeles, Calif.). The solution is changed to about 0.1 M sodium carbonate (pH 8.6) by dialysis versus 1 L of this buffer at 4° C. for 18 hours with 3 changes. The R1E4 antibody is derivatized with biotin by mixing 2 ml dialyzed antibody at 2 mg/ml with 400 $\mu$l Sulfo-NHS-biotin (Pierce Chemical Co., Rockford, Ill.) dissolved at 1 mg/ml in water. The antibody plus NHS-biotin reacted at ambient temperature for 2 hours. The unreacted biotin is removed by placing the reaction mixture in a Spectra/Por dialysis bag (14,000 MW cut-off) and dialyzed against 1 liter phosphate buffered saline (PBS). The dialysis solution is changed 3 times over an 18 hour period at 4° C. Biotinylated R1E4 is stored at −80° C. at about 2.5 mg/ml.

ASSAY A

ELISA (enzyme linked immunosorbant assay) measurements of IgE are as follows. About 5 $\mu$g of B1E3 antibody in 100 $\mu$l borate buffered saline (pH8.5) is added to wells of a NuncImmulon II 96 well plate (DiRuscio & Assoc., St. Louis, Mo.) at 37° C. for 90 minutes. The non-bound antibody is removed by flicking the plate. Unreacted sites on the plastic plate are blocked by adding about 200 $\mu$l of a 2% solution of newborn bovine serum (NBS) in PBS at 37° C. for 60 minutes. The standard IgE (or an unknown murine serum sample) is diluted to between about 4 ng/ml–256 ng/ml in Hanks - HS (20 mM Hepes, 2% NBS in Hanks Balanced Salt Solution, Gibco, Grand Island, N.Y.) or to 1/200 to 1/1000 in Hanks-HS respectively. 100 $\mu$l of standard (or unknown dilutions) are added in triplicate to the wells of the plate and allowed to absorb to B1E3 antibody at about 37° C. for 2–4 hours. The solution is removed by flicking the plate and each well is washed with about 0.5 ml 0.05% Tween 20-PBS 5 times. About 100 $\mu$l of biotinylated R1E4, called the primary antibody, diluted to 200 ng/ml is added to all wells and incubated at about 4° C. overnight. The solution is removed by flicking the plate and washed 5 times as described above. The developing reagent (Avidin and biotin-horse radish peroxidase) is incubated in 2% NBS in PBS at ambient temperature for 30 minutes, according to manufacturer's specifications (Vector Laboratories, Burlingame, Calif.). About 100 $\mu$l of developing reagent is added to each well and incubated at ambient temperature for 30 minutes. Colorimetric substrate for the developing reagent (ABTS peroxidase substrate system, KPL, Gaithersburg, Md.) is prepared by mixing equal volumes of solutions A and B and incubating at ambient temperature for 60 minutes. The developing reagent solution is removed by flicking the plate and washed 5 times as described above. Above 100 $\mu$l of the mixture of substrates is added to each well and incubated at ambient temperature for 60 minutes. The optical density of each well is determined on a BioTek ELISA reader (Biotek Instruments, Inc., Burlington, Vt.) and the absorbance data transferred electronically to a DEC VAX mainframe computer. A standard curve is fitted to the IgE standard optical densities using straight line, linear regression statistical fits. IgE in the unknown serum samples is determined by comparing the optical density of the unknown to the standard curve and multiplying that number by the dilution of serum used in the assay.

ASSAY B

Mouse IgG1 measurement by a two site sandwich ELISA is as follows. About 5 $\mu$g of rabbit anti mouse IgG (Organon-Teknika-Cappel, Malvern, Pa.) is attached to the wells of a NuncImmulon 96 well plate and IgG1 levels are determined in substantial accordance with Assay A except with the following changes. The IgG1 standard is purchased from Southern BioTech, Birmingham, Ala., and stored at 10 $\mu$g/ml in 2% NBS in PBS at 4° C. The standard curve is prepared by diluting the mouse IgG1 standard in 0.05% Tween-80 in PBS, and is linear between 3.9 and 250 ng/ml. Serum containing IgG1 is diluted 1/10,000 to 1/1,000,000 in 0.05% Tween 80-PBS, to place the measurement within the standard curve. Standard IgG1 (or diluted serum) is incubated at about 37° C. for 1 hour and the plates are washed with 0.05% Tween 80-PBS as described in Assay A. About a 1/3,000 dilution of Goat anti mouse IgG1 (Southern Biotech, Birmingham, Ala.) conjugated to alkaline phosphatase in 0.05% Tween 80-PBS is added to each well and incubated at about 37° C. for 60 minutes. The plate is washed and colorimetric substrate, prepared as described by the manufacturer (Alkaline Phosphatase Substrate System, KPL, Gaithersburg, Md.), is added and optical density and data analysis is performed in the same manner as Assay A.

ASSAY C

Measurement of mouse IgG2a by a two site sandwich ELISA is performed in substantial accordance with the teaching of Assay B except with the following changes. NuncImmulon II plates are used in this assay. The IgG2a standard is purchased from Southern Biotech. The standard curve is linear between 4–250 ng/ml. Serum containing IgG2a is diluted 1/6400 to 1/1,000,000. About a 1/6,000 dilution of goat anti mouse IgG2a (Southern Biotech) conjugated to alkaline phosphatase is used.

ASSAY D

Measurement of mouse IgG3 by a two site sandwich ELISA is performed in substantial accordance with the teaching of Assay B except for the following changes. About 25 ng of rabbit anti mouse IgG3 (Zymed Laboratories, San Francisco, Calif.) is attached to NuncImmulon 96 well plates. The IgG3 standard is purchased from Southern Biotech. The standard curve is linear between 1-62 ng/ml. Serum containing IgG3 is diluted 1/60,000 to 1/1,000,000. About a 1/6000 dilution of goat anti mouse IgG3 (Southern Biotech) conjugated to horse radish peroxidase is used as a combined primary antibody and developing reagent. 100 μl is added to each well and the plate incubated for 60 minutes at 37° C. The colorimetric substrate is prepared and used as described in Assay A.

ASSAY E

Measurement of mouse IgM by a two site sandwich ELISA is performed in substantial accordance with the teachings of Assay B except for the following changes. About 250 ng of rabbit anti-mouse IgM (Zymed Laboratories) is used to coat a NuncImmulon 96 well plate. The IgM standard is purchased from Southern Biotech. The standard curve is linear between 8-500 ng/ml. Serum containing IgM is diluted 1/4,000 to 1/60,000. About a 1/10,000 dilution of goat anti mouse IgM conjugated to horse radish peroxidase is used as a combined primary antibody and developing reagent. 100 μl is added to each well and the plate is incubated at about 4° C. overnight. The colorimetric substrate is prepared and used as described in Assay A.

ASSAY F

Stimulation of a transient serum IgE response in mouse with two monoclonal antibodies directed against IgD is carried out as follows.

Mouse hybridoma cells expressing either FF1-4D5 antibody or HaA1 antibody are thawed, established in culture, and incubated in CB6 F1 female mice as an ascites tumor and each immunoglublin is purified from the ascites fluid as described above. Both antibodies, stored separately, are dialyzed and concentrated at about 5 mg/ml in PBS. Antibodies are stored at −20° C.

A group of 4-5 Balb/c female mice (Charles River, Wilmington, Mass.) are maintained on water and chow ad librium. Individual mice between the age of 10-20 weeks are tagged with an ear label (National Band and Tag, Newport, Ky.) On day 0 each mouse receives about a 250-500 μl injection (mixture of 100 μg FF1-4D5 antibody and 100 μg HaA1 antibody dissolved in PBS) intravenously or subcutaneously. The mice are immobilized in a plastic shield with a slit for their tail to pass through. The tail vein is dilated with a swab of xylene and injected using a 28½ gauge needle attached to a 1cc syringe.

On days −1 (preimmune), 7, 8, 9 and 11, about 50-100 μl of serum is recovered separately from each mouse by puncturing the retroorbital venous sinus cavity. The mice are immobilized by tightly gripping the skin around the neck. Pressure is applied with a finger placed under the eye, causing the blood to pool in the retroorbital venus sinus cavity. An 18-22 gauge needle is used to puncture the vein. The drops of blood are collected by gravity into a 1.5 ml microtainer tube. The blood is permitted to coagulate at about 4° C. for 20 minutes to 4 hours. The clot is removed by centrifugation in an Eppendorf centrifuge at 500 rpm for about 20 minutes at 4° C. The serum in the supernatant is removed and transferred to a clean 1.5 ml polypropylene conical tube as described above.

Serum samples are stored, coded by mouse number from ear tag and day of bleed, at −20° C. Samples are diluted and IgE concentration determined by Assay A. Table 1 shows the mean IgE concentration of 4 treated mice on days −1 (Pre-treatment as background). The data indicate that IgE production peaks around eight days after injection of the immunostimulant.

TABLE 1

| Day | IgE ± SD (ng/ml) |
|-----|------------------|
| −1  | 1,135 ± 57       |
| 7   | 23,303 ± 2572    |
| 8   | 38,717 ± 1814    |
| 9   | 12,846 ± 4738    |
| 11  | 3,570 ± 865      |

EXAMPLE 13

Nine groups of 4 Balb/c female mice per group are injected with 100 μl FF1-4D 5 antibody and 100 μl HaA1 antibody on day 0 in accordance with Assay F. On day 3 and 4 individual groups receive at 7 a.m., 1 p.m. and 11 p.m. 250 μl of the indicated dose of (±)methyl 11α,16-dihydroxy-16-methyl-9-oxoprosta-5Z,13E-dien-1-oate dissolved in PBS injected peritoneally (IP) within 5 mm of the nipple with a 28½gauge syringe. Group A is a control without any prostaglandin. Group B is a control which was injected by PBS alone. Group C is a control which was injected by 0.01% ethanol alone. Group D is a control which was injected by PBS on Day 0 and 20 μg of the prostaglandin on Day 3 and 4. 2 μg (Group E), 5 μg (Group F), 10 μg (Group G), 20 μg (Group H) or 40 μg (Group I) of the prostaglandin is injected into the respective groups.

On day −1 and 8, 50-100 μl of serum is recovered separately from each mouse in substantial accordance with Assay F. Serum IgE levels are determined in substantial accordance with Assay A. Inhibition of serum IgE synthesis by (±) methyl 11α,16-dihydroxy-16-methyl-9-oxoprosta-5Z,13E-dien-1-oate at different doses are shown in Table 2. The data show that the prostaglandin of this invention reduces IgE production in a dose dependent manner. The data further show that a dose of 2 μg is sufficient to cause a significant reduction (about 62% less) in IgE production and that a dose between 20 μg and 40 μg is sufficient to keep IgE production at normal levels.

TABLE 2

| | Mean IgE ± SD (ng/ml) | | | |
|---|---|---|---|---|
| Day of Bleed | Group A 0 μg | Group B 0 μg | Group C 0 μg | Group D 40 μg |
| −1 | 1340 ± 217 | 1548 ± 762 | 1343 ± 308 | 1289 ± 10 |
| 8 | 14083 ± 610 | 15890 ± 4241 | 14478 ± 1345 | 1026 ± 387 |
| Day of Bleed | Group E 2 μg | Group F 5 μg | Group G 10 μg | Group H 20 μg | Group I 40 μg |
| −1 | 1294 ± 232 | 1292 ± 185 | 1382 ± 135 | 1308 ± 204 | 1114 ± 324 |
| 8 | 5401 ± 883 | 5076 ± 378 | 2661 ± 504 | 1608 ± 272 | 1217 ± 344 |

EXAMPLE 14

Five groups of 4 Balb/c female mice per group are injected with 100 μg FF1-4D5 antibody and 100 μg HəA1 antibody on Day 0 as described in Assay F. On day 1 and 2 (Group A), day 2 and 3 (Group B), day 3 and 4 (Group C), day 4 and 5 (Group D) received IP injections of 5 μg (±) methyl 11α,16-dihydroxy-16-methyl-9-oxoprosta-5Z,13E-dien-1-oate as described in Example 13. An untreated control is Group E. The results are shown in Table 3. IgE production is inhibited optimally when administered on day 3 and 4. The data show that regardless on what day the prostaglandin was administered IgE production (synthesis) was inhibited. The data also indicate that IgE production was still suppressed even after 11 days.

TABLE 3

| | | Serum IgE ± SD (ng/ml) | | | |
|---|---|---|---|---|---|
| Group | Day of Admin.* | Day −1 | Day 8 | Day 9 | Day 11 |
| A | 1, 2 | 1344 ± 135 | 9753 ± 4566 | 10678 ± 8402 | 2355 ± 709 |
| B | 2, 3 | 1293 ± 88 | 6233 ± 1948 | 5328 ± 1811 | 2139 ± 396 |
| C | 3, 4 | 1517 ± 166 | 4683 ± 1247 | 4505 ± 1155 | 1865 ± 361 |
| D | 4, 5 | 1644 ± 560 | 7969 ± 1821 | 7145 ± 1763 | 2316 ± 496 |
| E | None | 1363 ± 159 | 19549 ± 4166 | 17498 ± 5076 | 5317 ± 831 |

*(±) methyl 11α,16-dihydroxy-16-methyl-9-oxoprosta-5Z,13E-dien-1-oate

EXAMPLE 15

Ten groups of 4 Balb/c female mice per group are stimulated for IgE synthesis on day 0 by injection of FF1-4D5 antibody and HəA1 antibody as described in Assay F. On day 3 and 4 individual groups are injected IP with 1.0 μg (Group B), 2.0 μg (Group C), 10.0 μg (Group D), 40 μg (Group E) of (±) methyl 11α,16-dihydroxy-16-methyl-9-oxoprosta-5Z,13E-dien-1-oate at 7 a.m., and 7 p.m. or 0.5 μg (Group F), 1.0 μg (Group G), 2.0 μg (Group H), 10.0 μg (Group I) or 40.0 μg (Group J) of (±) methyl 11α,16-dihydroxy-16-methyl-9-oxoprosta-5Z,13E-dien-1-oate at 7 a.m, 1 p.m., 7 p.m. and 11 p.m. Group A is an untreated control. Individual mice are bled and serum IgE concentrations measured by Assay A. The results are shown in Table 4. The data indicate that (±) methyl 11α, 16-dihydroxy-16-methyl-9-oxoprosta-5Z, 13E-dien-1-oate is equally effective at inhibiting IgE production in a dose dependent manner whether administered 3 times a day or 4 times a day. The data further indicated that some inhibition is obtained at the lowest dosage of 1.0 μg and that the maximum inhibition is obtained at the highest dosage of 40.0 μg.

TABLE 4

| | | Serum IgE ± SD (ng/ml) | | | | |
|---|---|---|---|---|---|---|
| Group | Dose* | Day −1 | Day 7 | Day 8 | Day 9 | Day 11 |
| A | 0.0 | 800 ± 10 | 8850 ± 408 | 7557 ± 305 | 6458 ± 224 | 1466 ± 287 |
| B | 1.0 | 808 ± 17 | 4974 ± 1232 | 4595 ± 663 | 4602 ± 771 | 1326 ± 241 |
| C | 2.0 | 800 ± 10 | 5598 ± 1875 | 3057 ± 331 | 3644 ± 1179 | 1279 ± 377 |
| D | 10.0 | 849 ± 77 | 3223 ± 1717 | 1705 ± 859 | 1233 ± 601 | 1116 ± 276 |
| E | 40.0 | 822 ± 39 | 998 ± 146 | 1214 ± 181 | 1119 ± 135 | 1110 ± 249 |
| F | 0.5 | 839 ± 44 | 7813 ± 588 | 5699 ± 322 | 6097 ± 249 | 2049 ± 1201 |
| G | 1.0 | 1197 ± 272 | 5549 ± 1044 | 3051 ± 475 | 4383 ± 832 | 1506 ± 794 |
| H | 2.0 | 1019 ± 206 | 5483 ± 717 | 3236 ± 599 | 3987 ± 401 | 1925 ± 410 |
| I | 10.0 | 1040 ± 211 | 2092 ± 605 | 1884 ± 598 | 1991 ± 834 | 1429 ± 361 |
| J | 40.0 | 929 ± 97 | 1037 ± 237 | 1152 ± 388 | 870 ± 83 | 1028 ± 302 |

*(±) methyl 11α,16-dihydroxy-16-methyl-9-oxoprosta-5Z,13E-dien-1-oate

EXAMPLE 16

Sera from the mice described in Example 13 are analyzed for the levels of IgG1, IgG2a, and IgG3 by Assays B, C, and D, respectively. The results are shown in Table 5. The data show that the prostaglandins of the invention have essentially no effect upon IgG1, IgG2a and IgG3 levels.

TABLE 5

| | | Ig ± SD (μg/ml) | | | |
|---|---|---|---|---|---|
| Group | Day −1 | Day 7 | Day 8 | Day 9 | Day 11 |
| | | | IgG1 | | |
| A | 222 ± 133 | 4808 ± 1917 | 13818 ± 1281 | 17700 ± 4149 | 17100 ± 3875 |
| E | 215 ± 124 | 3220 ± 985 | 12947 ± 2195 | 19938 ± 3279 | 17589 ± 1923 |
| F | 248 ± 189 | 6902 ± 3604 | 18202 ± 5327 | 27069 ± 3257 | 23205 ± 6506 |
| G | 166 ± 14 | 6952 ± 3410 | 17649 ± 3158 | 26978 ± 11752 | 26361 ± 6660 |
| H | 255 ± 66 | 6816 ± 3349 | 16838 ± 4174 | 23900 ± 11791 | 24998 ± 7169 |
| I | 175 ± 32 | 5168 ± 2391 | 15666 ± 2300 | 24337 ± 4729 | 25930 ± 4376 |
| | | | IgG2a | | |
| A | 23 ± 3 | 139 ± 72 | 554 ± 247 | 923 ± 69 | 951 ± 163 |
| E | 25 ± 25 | 114 ± 61 | 277 ± 111 | 1053 ± 256 | 1124 ± 219 |
| F | 58 ± 66 | 133 ± 67 | 481 ± 192 | 1093 ± 245 | 1540 ± 201 |
| G | 26 ± 7 | 107 ± 45 | 276 ± 168 | 855 ± 117 | 1097 ± 289 |
| H | 29 ± 9 | 182 ± 105 | 493 ± 187 | 1170 ± 285 | 2133 ± 862 |
| I | 23 ± 1 | 81 ± 12 | 433 ± 314 | 1177 ± 383 | 1667 ± 675 |
| | | | IgG3 | | |
| A | 66 ± 3.6 | 227 ± 61 | 519 ± 145 | 510 ± 169 | 465 ± 118 |
| E | 70 ± 10 | 370 ± 229 | 882 ± 310 | 741 ± 475 | 687 ± 152 |
| F | 109 ± 44 | 464 ± 161 | 640 ± 46 | 649 ± 232 | 559 ± 162 |
| G | 68 ± 2 | 494 ± 267 | 789 ± 264 | 760 ± 340 | 802 ± 216 |
| H | 77 ± 10 | 446 ± 266 | 1075 ± 453 | 1636 ± 275 | 1288 ± 156 |

TABLE 5-continued

| Group | Day −1 | Day 7 | Day 8 | Day 9 | Day 11 |
|---|---|---|---|---|---|
| | | | Ig ± SD (µg/ml) | | |
| I | 68 ± 6.5 | 236 ± 84 | 639 ± 104 | 1048 ± 167 | 1044 ± 115 |

Two groups of 4 Balb/c female mice per group are injected with both 100 µg FF1-4D5 antibody and 100 µg Hðal antibody. On day 3 and 4 the mice are injected with PBS (Group A) or 20 µg (±) methyl 11α,16-dihydroxy-16-ethyl-9-oxoprosta-5Z,13E-dien-1-oate (Group B) at 7 a.m., 1 p.m. and 7 p.m. in substantial accordance with the teaching of Example 13. On day −1, 7, 8, 9 and 11, 50–100 µl of serum is recovered and analyzed for IgE by Assay A and for IgM by Assay E. The results are shown in Table 6. The data show that IgE production is fully inhibited while IgM synthesis is not affected.

TABLE 6

| Group | Day −1 | Day 7 | Day 8 | Day 9 | Day 11 |
|---|---|---|---|---|---|
| | | IgE ± SD (ng/ml) | | | |
| A | 853 ± 101 | 4545 ± 335 | 11398 ± 4689 | 7114 ± 2317 | 1064 ± 318 |
| B | <800 | 847 ± 67 | 1264 ± 173 | 1064 ± 106 | 808 ± 16 |
| | | IgM ± SD (µg/ml) | | | |
| A | 234 ± 38 | 1488 ± 314 | 1690 ± 338 | 1396 ± 421 | 548 ± 87 |
| B | 272 ± 19 | 1858 ± 107 | 2569 ± 803 | 2104 ± 276 | 725 ± 199 |

EXAMPLE 18

This example demonstrates that (±) methyl 11α,16-dihydroxy-16-methyl-9-oxoprosta-5Z,13E-dien-1-oate does not effect basal cell surface density or distribution of leukocyte membrane proteins involved in immune recognition and regulation in unstimulated mice. One group of 4 unstimulated Balb/c female mice is injected with PBS (Group A). Another (Group B) is injected with 20 µg (±) methyl 11α,16-dihydroxy- 16-methyl-9-oxoprosta-5Z,13E-dien-1-oate as in Example 13. After 3 days, the mice are sacrificed by cervical dislocation. A 3 cm incision is made with a scalpel above the left hip, and the spleen is cut free from adjoining tissue and placed in a 100 mn plastic culture dish containing 10 ml PBS. The splenic cells are then made into a suspension, by rubbing the spleens between the rough, frosted ends of microscope slides repeatedly until the only remaining particulate matter is connective tissue. Cells are transferred to a 15 ml conical polystyrene tube and centrifuged in a centrifuge at 1200 rpm for 5 minutes. The supernatant is discarded by aspiration and the cell pellet is resuspended in 10 ml PBS, then centrifuged at 1200 rpm for 5 minutes. The supernatant is aspirated and the cell pellet is resuspended in 15 mM Tris, 140 mM Ammonium Chloride, to lyse red blood cells. After incubating at room temperature for 10 minutes the cell suspension is centrifuged at 1200 rpm for 10 minutes. The supernatant is discarded and the cell pellet is resuspended in 10 ml FACS Buffer (PBS containing 0.1% BSA and 0.1% Sodium Azide). The cell suspension is filtered through sterile glass wool plugged in the top of a pasteur pipet. Cells in the flow through are counted using a hemacytometer, then the cell suspension is centrifuged at 1200 rpm for 5 minutes. The supernatant is discarded and the cell pellet is resuspended in a volume of FACS Buffer that will yield $4 \times 10^7$ cells/ml. 10 µl ($4 \times 10^5$ cells) is added to each well of a 96-well V-bottom plate. 25 µl of diluted monoclonal antibody directed against splenocyte cell surface proteins is added to each well: Major Histocompatability Complex (MHC) Class II (M5114, ATCC, Rockville Maryland), MHC Class I (M1/42, ATCC), Anti-IgD (JA12.5, ATCC, Rockville, MD), Thymocyte (Thy)-1 (JIJ, ATCC), B220 (14.8, ATCC), Kappa light chain (187, ATCC), IL-2 Receptor (7D4, ATCC), Lyt-1 (7.313, ATCC) and CD23 (biotinylated B3B4) and incubated on ice for 30 minutes. 100 µl 10% BSA 0.1% sodium azide is added to each well, then the plates are centrifuged at 1200 rpm for 10 minutes. The liquid is removed by aspiration and the cell pellets are resuspended in 100 µl FACS Buffer, and centrifuged at 1200 rpm for 5 minutes. The supernatant is removed by aspiration and the cells are resuspended in 25 µl secondary antibody as follows: For MHC Class II, MHC Class I, Anti-IgD, Thy-1, B220, Kappa light chain, IL-2 Receptor, Lyt-1 the secondary antibody is a mixture of FITC conjugated rat monoclonal antibodies, RG711.1 and RG9.1 (ATCC). For CD23, the secondary reagent is FITC labelled Avidin (Vector Laboratories, Burlingame, CA). After incubating the cells with the secondary antibody for 30 minutes on ice, 100 µl 10% BSA 0.1% sodium azide is added to each well, then centrifuged at 1200 rpm for 10 minutes. Cells are resuspended in 100 µl FACS buffer then centrifuged at 1200 rpm for 5 minutes. The supernatant is removed by aspiration and cells are resuspended in 50 µl FACS buffer. A FACScan Flow cytometer (Becton Dickinson, Mountain View, CA) is used. The instrument was equilibrated using an AutoComp program (Becton Dickinson, Mountain View, CA). Samples are transferred to individual tubes and 10,000 cells are analyzed. Using the Lysis software (Becton Dickinson, Mountain View, CA) the means channel log flourescence and percent positive cells are determined for the entire cell population. As shown in Table 7, the (±) methyl 11α,16-dihydroxy-16-ethyl-9-oxoprosta-5Z,13E-dien-1-oate treated group displayed identical cell surface density and distribution as the control group.

TABLE 7

| Cell Surface Protein | Mean Channel Log Fluorescence | | Percentage Positive Cells | |
|---|---|---|---|---|
| | Group A | Group B | Group A | Group B |
| MHC Class II | 148 ± 30 | 149 ± 8 | 56.2 ± 4 | 56.9 ± .4 |
| MHC Class I | 112 ± 3.5 | 113 ± 2 | 57.8 ± 14.9 | 79 ± 16 |
| IgD | 130 ± 4 | 132 ± 3.5 | 1.4 ± 3 | 51.8 ± 3.7 |
| Thy 1 | 91 ± 0 | 92 ± 3 | 9.3 ± 2.6 | 25.4 ± 3 |
| B220 | 104 ± 43 | 105 ± 2.5 | 49.6 ± 1.6 | 50.6 ± 4.6 |
| κ Light Chain | 135 ± 3.7 | 131 ± 4 | 52.1 ± 3.9 | 53.9 ± 2.1 |
| Lyt 1 | 110 ± 3.2 | 117 ± 6 | 31 ± 6.4 | 44.5 ± 7 |
| IL-2 receptor | 98 ± 1.7 | 96 ± 1 | 2.4 ± 0.6 | 2.7 ± 0.3 |
| CD23 | 95 ± 5 | 94 ± 3.2 | 46.6 ± 4.4 | 44.2 ± 6.6 |

EXAMPLE 19

This example demonstrates that (±) methyl 11α, 16-dihydroxy-16-methyl-9-oxoprosta-5Z,13E-dien-1-oate does not effect cell surface density or distribution of leukocyte membrane proteins involved in immune recognition and regulation in mice stimulated with FF1-4D5 antibody and HƏA1 antibody Two (2) groups of 4 Balb/c female mice are injected with both 100 μg FF1-4D5 antibody and 100 μg HƏA1 antibody on day 0 in accordance with the procedure of Example 13. On day 3 and 4 the mice are injected with PBS (Group A) or injected with 20 μg (±) methyl 11α, 16-dihydroxy-16-methyl-9-oxoprosta-5Z, 13E-dien-1-oate (Group B) as in Example 13. On day 7 the mice are sacrificed by cervical dislocation and the splenocytes harvested and stained for leukocyte proteins in substantial accordance with the teaching of Example 18. As shown in Table 8, the (±) methyl 11α,16-dihydroxy-16-methyl-9-oxoprosta-5Z,13E-dien-1-oate treated group displayed identical cell surface density and distribution as the PBS treated group.

TABLE 8

| Cell Surface Protein | Mean Channel Log Fluorescence | | Percentage Positive Cells | |
|---|---|---|---|---|
| | Group A | Group B | Group A | Group B |
| MHC Class II | 134 ± 8 | 137 ± 15 | 59.8 ± 1.5 | 68.6 ± 5.1 |
| MHC Class I | 113 ± 3.6 | 121 ± 15 | 48.5 ± 12.3 | 59.4 ± 5.4 |
| IgD | 107 ± 4.9 | 98 ± 0.5 | 21.9 ± 8.4 | 15.6 ± 8.4 |
| Thy I | 97 ± 0.5 | 98 ± 0 | 14.3 ± 2.5 | 23 ± 10 |
| B220 | 107 ± 1 | 112 ± 4 | 49.3 ± 4.3 | 61.2 ± .9 |
| K Light Chain | 118 ± 3.5 | 119 ± 7 | 50 ± 5.3 | 58 ± 14.6 |
| Lyt 1 | 110 ± 1 | 109 ± 2 | 31.3 ± 1.2 | 30.4 ± 8.8 |
| IL-2 receptor | 101 ± 1 | 97 ± 1.5 | 18.4 ± 2.5 | 23 ± 7.7 |
| CD23 | 99 ± 1 | 95 ± 1.5 | 20.4 ± 5.4 | 11.6 ± 1.6 |

EXAMPLE 20

This example demonstrates that de nouo IgE synthesis is inhibited by (±) methyl 11α,16-dihydroxy-16-methyl-9-oxoprosta-5Z,13E-dien-1-oate in vivo, but not by natural prostaglandin $E_1$ and prostaglandin $E_2$ in vivo. Four groups of 4 Balb/c female mice per group are injected with 100 μg FF1-4D5 antibody and 100 μg HƏA1 antibody on Day 0. On day 3 and 4, Group B is injected with 20 μg (±) methyl 11α,16-dihydroxy-16-methyl-9-oxoprosta-5Z,13E-dien-1-oate, Group C is injected with 20 μg prostaglandin $E_1$ (Biomol Research Laboratories, Inc., Plymouth Meeting, PA) and Group D is injected with 20 μg prostaglandin $E_2$ (Biomol Research Laboratories, Plymouth Meeting, PA) as described in Example 13. Group A is an untreated control. On day −1 and 8, 50–100 μg of serum is recovered and analyzed for IgE by Assay A. The results are shown in Table 9. The data shows the inhibition of IgE by (±) methyl 11α,16-dihydroxy-16-methyl-9-oxoprosta-5Z,13-dien-1-oate and the lack of inhibition by prostaglandin $E_1$ (PGE$_1$) and prostaglandin $E_2$ (PGE$_2$).

TABLE 9

| Group | IgE ± SD (ng/ml) | |
|---|---|---|
| | Day −1 | Day 8 |
| A | <800 | 3539 ± 499 |
| B | 1015 ± 70 | 1206 ± 119 |
| C | <800 | 2958 ± 717 |
| D | 897 ± 194 | 3340 ± 384 |

EXAMPLE 21

This example demonstrates inhibition of de novo IgE synthesis by (±) methyl 11α,16-dihydroxy-16-methyl-9-oxoprosta-5Z,13E-dien-1-oate when orally administered and that natural PGE$_2$ is ineffective.

Three groups of a 4 Balb/c female mice per group are injected with both 100 μg FF1-4D5 antibody and 100 μg HƏA1 antibody (Groups B,C, and D). Another group of 4 Balb/C female mice is injected with PBS alone, unstimulated control Group A. One of the stimulated group were not given any prostaglandin control Group B. On day 3 and 4, individual groups receive an intragastric feeding TID of 0.25 ml of 20 μg of (±) methyl 11α,16-dihydroxy-16-methyl-9-oxoprosta-5Z,13E-dien-1-oate (Group C) or 20 μg of prostaglandin $E_2$ (Group D) dissolved in PBS. On day −1, 8, and 10, 50–100 μl of serum is recovered and analyzed for IgE by Assay A. The results are shown in Table 10. The data show that (±) methyl 11α,16-dihydroxy-16-methyl-9-oxoprosta-5Z,13E-dien-1-oate significantly inhibits de novo IgE synthesis after oral administration, but that natural prostaglandin $E_2$ inhibits IgE synthesis slightly, if at all.

TABLE 10

| Group | IgE ± SD (ng/ml) | | |
|---|---|---|---|
| | Day −1 | Day 8 | Day 10 |
| A | 1053 ± 90 | 1015 ± 61 | 1059 ± 143 |
| B | 1067 ± 18 | 5792 ± 1514 | 1498 ± 124 |
| C | 1115 ± 201 | 1490 ± 525 | 1131 ± 198 |
| D | 1094 ± 107 | 3724 ± 1361 | 1496 ± 219 |

EXAMPLE 22

This example demonstrates that (±) methyl 11α, 16-dihydroxy-16-methyl-9-oxoprosta-4Z,13E-dien-1-oate inhibits de novo IgE synthesis but does not effect IgG1 or IgG2a. Two groups of 4 Balb/c female mice per group are injected with both 100 μg FF1-4D5 antibody and 100 μg HβA1 antibody. One of these groups is a stimulated control designated Group B. On day 3 and 4, the other group is injected with 40 μg (±) methyl 11α, 16-dihydroxy-1methyl-9-oxoprosta-4Z,13E-dien-1-oate. Another group is injected with only PBS as an unstimulated control (Group A). On day −1 and 8, 50–100 μl of serum is recovered and analyzed for IgE, IgG1 and IgG2a by Assays A, B, and C, respectively. The results are shown in Table 11. The data show that (±) methyl 11α, 16-dihydroxy-16-methyl-9-oxoprosta-4Z,13E-dien-1oate inhibits de novo IgE synthesis, but does not effect IgG1 of IgG2a.

TABLE 11

| Group | Day −1 | Day 8 |
|---|---|---|
| | IgE ± SD (ng/ml) | |
| A | 384 ± 242 | 1420 ± 156 |
| B | 1548 ± 762 | 15890 ± 4241 |
| C | 1717 ± 313 | 3973 ± 905 |
| Group | Day −1 | Day 9 |
| | IgG1 ± SD (μg/ml) | |
| A | 863 ± 743 | 767 ± 670 |
| B | 344 ± 89 | 19800 ± 6139 |
| C | 2331 ± 2212 | 37728 ± 6913 |
| | IgG2a ± SD (μg/ml) | |
| A | 61 ± 39 | 79 ± 74 |
| B | 109 ± 97 | 1056 ± 116 |
| C | 160 ± 130 | 1058 ± 202 |

EXAMPLE 23

This example demonstrates that (±) methyl 2-[2-[3R-3a-hydroxy-2β-(4-hydroxy-4-methyl-1E-octenyl)-5- oxo-1α-cyclopentyl]-methyl]cyclopropanebutanoate and (±) methyl 2-[2-[3R-3a-hydroxy-2β-(4-hydroxy-4-methyl-1E-octenyl)-5-oxo-1α-cyclopentyl)-methyl]cyclopropanebutanoate and (±) methyl 2-[2-[3R-3α-hydroxy-2β-(4-hydroxy-4-methyl-1E-octenyl)- 5-oxo-1α-cyclopentyl]ethyl]cyclopropanepropanoate inhibit de novo IgE synthesis, but not IgG1, IgG2a or IgG3. 3 groups of 4 Balb/c female mice per group are injected with both 100 μg FF1-4D5 antibody and 100 μg HəA1 antibody on day 0. Group A is given no further treatment. On day 3 and 4, one group of mice is injected with 20 μg (±) methyl 2-[2-[3R-3α-hydroxy-2β-(-b 4-hydroxy-4-methyl-1E-octenyl-5oxo-1α-cyclopentyl]-methyl]cyclopropanebutanoate (Group B) and another group with 20 μg (±) methyl 2-[2-[3R-3α-hydroxy-2β-(4-hydroxy-4-methyl-1E-octenyl)-5-oxo-1β-cyclopentyl]ethyl]cyclopropanepropanoate (Group C) as in Example 13. On day −1 and 8, 50-100 μl of serum is recovered and analyzed for IgE, IgG1, IgG2a and IgG3 by Assays A, B, C and D, respectively. The selectivity

EXAMPLE 25

This example demonstrates that (±) methyl 11 α,16-dihydroxy-4,4,16-trimethyl-9-oxoprost-13E-en-1-oate and (±) methyl-11 α,16-dihydroxy-16-methyl-9-oxoprost-3,5Z,13E-trien-1-oate inhibit de novo IgE synthesis, but not IgG1, IgG2a, IgG3 and IgM. Three groups of 5 Balb/c female mice per group are injected with both 100 μg FF1-4D5 antibody and 100 μg HəA1 antibody on day 0. Group A is a control with no further treatment. On day 3 and 4, the mice are injected with 20 μg (±) methyl 11α,16-dihydroxy-4,4,16-trimethyl-9-oxoprosta-13E-en-1-oate (Group B) or 20 μg (±) methyl 11α,16-dihydroxy-16-methyl-9-oxoprosta-3,5Z,13E-trien-1-oate (Group C) as in Example 13. On day −1 and 8,50−00 μl of serum is recovered and analyzed for IgE, IgG1, IgG2a, IgG3 and IgM by Assays A, B,C,D and E, respectively. The selective inhibition of IgE by the prostaglandins of the invention is shown in Table 14.

TABLE 14

|  | IgE ± SD (ng/ml) | IgG1 ± SD (μg/ml) | IgG2a ± SD (μg/ml) | IgG3 ± SD (μg/ml) | IgM ± SD (μg/ml) |
|---|---|---|---|---|---|
| Day −1 All Groups | <800 | 859 ± 379 | 533 ± 364 | 215 ± 80 | 1534 ± 433 |
| Day 8 Group |  |  |  |  |  |
| A | 6071 ± 1700 | 21703 ± 3334 | 1246 ± 168 | 1538 ± 208 | 4147 ± 699 |
| B* | <800 | 22555 ± 5821 | 1019 ± 278 | 2103 ± 616 | 9792 ± 984 |
| C† | 1176 ± 137 | 18320 ± 4695 | 1202 ± 338 | 1709 ± 429 | 7708 ± 993 |

*(±) methyl 11α,16-dihydroxy-4,4,16-trimethyl-9-oxoprost-13E-en-1-oate
†(±) methyl 11α,16-dihydroxy-16-methyl-9-oxoprosta-3,5Z,13E-trien-1-oate of inhibition of IgE is shown in Table 12.

TABLE 12

|  | IgE ± SD (ng/ml) | IgG1 ± SD (μg/ml) | IgG2a ± (μg/ml) | IgG3 ± SD (μg/ml) |
|---|---|---|---|---|
| Day −1 All Groups | 51 ± 82 | 180 ± 92 | 43 ± 6 | 38 ± 21 |
| Day 8 Group |  |  |  |  |
| A | 11398 ± 4689 | 10525 ± 949 | 849 ± 304 | 584 ± 138 |
| B* | 2750 ± 318 | 14470 ± 2997 | 834 ± 235 | 520 ± 39 |
| C† | 3034 ± 878 | 22573 ± 5690 | 840 ± 484 | 901 ± 213 |

*(±) methyl 2-[2-[3R-3α-hydroxy-2β-(4-hydroxy-4-methyl-1E-octenyl)-5-oxo-1α-cyclopentyl)methyl]cyclopropanebutanoate
†(±) methyl 2-[2-(3R-3α-hydroxy-2β-(4-hydroxy-4-methyl-1E-octenyl)-5-oxo-1α-cyclopentyl)ethyl]-cyclopropanebutanoate

EXAMPLE 24

This example demonstrates that (±) methyl 20-ethyl-11α,16-dihydroxy-16-methyl-9-oxoprost-13E-en-1oate inhibits de novo IgE synthesis. Two groups of 5 Balb/c female mice per group are injected with both 100 μg FF1-4D5 antibody and 100 μg HəA1 antibody on day 0. One group is stimulated control (Group A). On day 3 and 4, the other group is injected with 20 μg (±) methyl 20-ethyl-11α,16-dihydroxy-16-methyl-9-oxoprost-13E-en-1-oate. On day −1and 8, 50-100 μl of serum is recovered and analyzed for IgE by Assay A. The inhibition of IgE is shown in Table 13.

TABLE 13

| | IgE ± SD (ng/ml) |
|---|---|
| Day −1 All Groups | <800 ng/ml |
| Day 8 Group | |
| A | 3653 ± 358 |
| B* | <800 |

(±) methyl 20-ethyl-11α,16-dihydroxy-1-methyl-9-oxoprost-13E-en-1-oate

EXAMPLE 26

This example demonstrates that (±) 11α,16-dihydroxy-16-methyl-9-oxoprost-13E-en-1oic acid and (±) 4-(acetylamino)phenyl 11α,16-dihydroxy-16-methyl-9-oxoprost-13E-en-1-oate inhibit de novo IgE synthesis. Three groups of 5 Balb/c female mice per group are injected with both 100 μg FF1-4D5 antibody and 100 μg HəA1 antibody on day 0. Group A is a control with no further treatment. On day 3 and 4, the mice are injected with 20 μg of (±) 11α,16-dihydroxy-16-methyl-9-oxoprost-13E-en-1-oic acid (Group B) and with 20 μg of (±) 4-(acetylamino)phenyl 11α, 16-dihydroxy-16-methyl-9-oxoprost-13E-en-1-oate (Group C). On day −1 and 8,50-100 μl of serum is recovered and analyzed for IgE by Assay A. Inhibition of IgE by these compounds is shown in Table 15.

TABLE 15

| | IgE ± SD (ng/ml) | |
|---|---|---|
| Group | Day −1 | Day 8 |
| A | 1073 ± 391 | 5090 ± 355 |
| B* | 1029 ± 362 | 1499 ± 132 |

TABLE 15-continued

| | IgE ± SD (ng/ml) | |
|---|---|---|
| Group | Day −1 | Day 8 |
| C† | <800 | 1880 ± 319 |

*(±) 11α,16-dihydroxy-16-methyl-9-oxoprost-13E-en-1-oic acid
†(±) 4-acetylamino)phenyl 11α,16-dihydroxy-16-methyl-9-oxoprost-13E-en-1-oate

EXAMPLE 27

This example demonstrates that (±) methyl 11α,16-dihydroxy-16-methyl-9-oxoprost-13E-en-1-oate, (±) methyl 11α,16-dihydroxy-16-methyl-9-oxoprostan-1-oate and (±) methyl ethyl 11α,16-dihydroxy-16-methyl-9-oxoprost-13E-en-1-oate inhibit de novo IgE synthesis. Four groups of 5 Balb/c female mice per group are injected with both 100 μg FF1-4D5 antibody and 100 μg H∂A1 antibody on day 0. One group is control Group A. On day 3 and 4, the mice are injected with 10 μg of (±) methyl 11α,16-dihydroxy-16-methyl-9-oxoprost-13E-en-1-oate (Group B), with 10 μg of (±) methyl 11α,16-dihydroxy-16methyl-9-oxoprostan-1-oate (Group C), or with 10 μg of (±) methylethyl 11α,16-dihydroxy-16-methyl-9-oxoprost-13E-en-1oate (Group D). On day −1 and 8, 50–100 μl of serum is recovered and analyzed for IgE by Assay A. Inhibition of IgE by these compounds is shown in Table 16.

TABLE 16

| | IGE ± SD (ng/ml) | |
|---|---|---|
| Group | Day −1 | Day 8 |
| A | <1600 | 8548 ± 1117 |
| B* | <1600 | 2123 ± 257 |
| C† | <1600 | 3844 ± 238 |
| D● | <1600 | 2127 ± 149 |

*(±) methyl 11α,16-dihydroxy-16-methyl-9-oxoprost-13E-en-1-oate
†(±) methyl 11α,16-dihydroxy-16-methyl-9-oxoprostan-1-oate
●(±) methyl ethyl 11α,16-dihydroxy-16-methyl-9-oxoprost-13E-en-1-oate

EXAMPLES 28

From the data in the above examples, the effective does of each prostaglandin to achieve 50% inhibition of OgE (ED$_{50}$) was calculated. The data show that eight of the compounds exhibit extraordinary high potency with dosages of only 1.0–1.5 μg/mouse to achieve 50% inhibition, whereas, natural prostaglandin E$_2$ requires a dosage of greater than 45 μg/mouse to achieve the same effect.

Since prostaglandins in general elicit diarrheal side effects in humans, some of these compounds were also evaluated for diarrheal effects in rats to determine their ability to cause this side effect. The data presented in Table 17 are ED$_{50}$ values defined as the dose required to produce diarrhea in 50% of the animals. The assay was performed as described in Collins et al., *J. Med. Chem.* 32, 1001(1989). Briefly, adult Charles River male rats weighing 210–230 g were individually housed and fasted with water available ad libitum for 24 hours prior to the test. The animals (N=6–12) received logarithmically graded prostaglandin doses orally. Immediately after administration, the animals were returned to their cages, and diarrhea, if any, was assessed on an all or none basis for 8 hours after drug treatment. The ED$_{50}$ and relative potency values were calculated by the logistic method of Berkson. The data show that (±) methyl-20-ethyl-11α,16-dihydroxy-16-methyl-9-oxoprost-13E-en-1-oate is essentially free of the undesirable diarrhea side-effect.

TABLE 17

| | ED$_{50}$ IgE Inhibition (μg/mouse/TID) | Diarrhea (μg/kg/Rat) |
|---|---|---|
| (±) 4-(acetylamino)phenyl 11α,16-dihydroxy-16-methyl-9-oxoprost-13E-en-1-oate | 1.0 | — |
| (±) methyl 11α,16-dihydroxy-16-methyl-9-oxoprosta-4Z,13E-dien-1-oate | 4.0 | 49 |
| (±) methyl 11α,16-dihydroxy-16-methyl-9-oxoprosta-5Z,13E-dien-1-oate | 1.0 | 173 |
| (±) methyl 11α,16-dihydroxy-16-methyl-9-oxoprost-13E-en-1-oate | 1.5 | 360 |
| (±) methyl 11α,16-dihydroxy-16-methyl-9-oxoprostan-1-oate | 4.8 | — |
| (±) 1-methylethyl 11α,16-dihydroxy-16-methyl-9-oxoprost-13E-en-1-oate | 1.5 | — |
| (±) 11α,16-dihydroxy-16-methyl-9-oxoprost-13E-en-1-oic acid | 1.0 | — |
| (±) methyl 2-[[3R-3α-hydroxy-2β-(4-hydroxy-4-methyl-1E-octenyl)-5-oxo-1α-cyclopentyl]methyl]cyclopropanebutanoate | 9.0 | — |
| (±) methyl 2-[2-(3R-3α-hydroxy-2β-(4-hydroxy-4-methyl-1E-octenyl)-5-oxo-1α-cyclopentyl]ethyl]cyclopropanepropanoate | 1.0 | — |
| (±) methyl 11α,16-dihydroxy-16-methyl-9-oxoprosta-3,5Z,13E-trien-1-oate. | 6.5 | 570 |
| (±) methyl 11α,16-dihydroxy-4,4,16-trimethyl-9-oxoprost-13E-en-1-oate | 1.5 | 185 |
| (±) methyl 20-ethyl-11α,16-dihydroxy-16-methyl-9-oxoprost-13E-en-1-oate | 1.0 | 2700 |
| Natrual Prostaglandin E$_2$ (PGE$_2$) | >45.0 | — |

EXAMPLE 29

Stimulation of a secondary antigen-specific IgE response in mouse with haptenated antigen absorbed on alum is inhibited by (±) methyl 11α,16-dihydroxy-16-methyl-9-oxoprosta-5Z,13E-dien-1-oate. Three groups of 7 Balb/c female mice were treated as follows. On day 0 all mice were injected IP, as in Example 13, with 1 μg of trinitrophenol-keyhole limpet hemocyanin (TNP-KLH) on 1 mg of alum, described in F. O. Finkelman et al., *The Journal of Immunology*, 141: 2335 (1988). On day 21, one group was given an intraperitoneal injection (IP) of PBS (Group A), and the other groups were given IP injections of 1 μg TNP-KLH on 1 mg alum. One of these groups was not given any further treatment (Group B). On days 24 and 25, the remaining group received on IP injection of 20 μg (±) methyl-11α,16-dihydroxy-16-methyl-9-oxoprosta-5Z,13E-dien-1-oate at 7 a.m., 1 p.m. and 7 p.m. (Group C). On day −1, 28 and 30, 50–100 μl of serum is recovered and analyzed for IgE by Assay A. The results are shown in Table 18. The data show a secondary IgE response in the boosted Group B mice, and no secondary IgE response in the control, non-boosted Group A mice. Mice that were boosted with antigen and treated with (±) methyl-11α,16-dihydroxy-16-methyl-9-oxoprosta-5Z,13E-dien-1-oate (Group C) were inhibited from the synthesis of a secondary IgE response.

TABLE 18

| Group | Day −1 | IgE ± SD (ng/ml) Day 28 | Day 30 |
|---|---|---|---|
| A | 1472 ± 231 | 4696 ± 2068 | 3245 ± 1635 |
| B | 1440 ± 88 | 28,568 ± 17,675 | 22,564 ± 12,587 |
| C | 1487 ± 138 | 14,448 ± 4926 (p < .02) | 7564 ± 1528 (p < .016) |

Although the invention has been described with respect to specific modifications, the details thereof are not to be construed as limitations, for it will be apparent that various equivalents, changes and modifications may be resorted to without departing from the spirit and scope thereof and it is understood that such equivalent embodiments are to be included therein.

What is claimed is:

1. (±) Methyl-20-ethyl-11α,16-dihydroxy-16-methyl-9-oxoprost-13E-en-1-oate.

* * * * *